United States Patent [19]

Kökösi et al.

[11] Patent Number: 4,472,399
[45] Date of Patent: Sep. 18, 1984

[54] INDOLO[2',3';3,4]PYRIDO[2,1-B]QUINAZO-LINE-5-ONES, A PROCESS FOR THE PREPARATION THEREOF, AND DIURETIC COMPOSITIONS AND METHODS USING THEM

[75] Inventors: Jozsef Kökösi, Budaörs; Istvan Hermecz, Budapest; Zoltan Meszaros, Budapest; Sandor Virag, Budapest; Lelle Vasvari, nee Debreczy, Budapest; Gyorgy Szasz, Budapest; Agnes Horvath, Budapest; Tibor Breining, Budapest; Tamas Szüts, Budapest; Gyula Sebestyen, Budapest, all of Hungary

[73] Assignee: Chinoin Gyogyszer es Vegyeszeti Termekek Gyara Rt., Budapest, Hungary

[21] Appl. No.: 308,037

[22] Filed: Oct. 2, 1981

[30] Foreign Application Priority Data

Jun. 24, 1980 [HU] Hungary .............................. 1555/80
Jun. 24, 1980 [HU] Hungary .............................. 1556/80

[51] Int. Cl.$^3$ .................. A61K 31/505; C07D 487/14
[52] U.S. Cl. ......................................... 424/251; 544/245
[58] Field of Search ............................ 544/245; 424/251

[56] References Cited

U.S. PATENT DOCUMENTS

| 2,858,251 | 10/1958 | Pachter et al. | 424/251 |
| 2,866,788 | 12/1958 | Pachter | 544/245 |
| 4,395,549 | 7/1983 | Hermecz et al. | 544/252 |

FOREIGN PATENT DOCUMENTS

| 889337 | 7/1981 | Belgium. | |
| 52-098 | 6/1977 | Japan | 544/245 |
| 52-099 | 6/1977 | Japan | 544/245 |

OTHER PUBLICATIONS

Kametani, et al., J. Am. Chem. Soc., 99, pp. 2306-2309, (1977).
Kametani, et al., J. Am. Chem. Soc., 98(20), pp. 6186-6188, (1976).
Kametani, Chemical Abstracts, vol. 91, 20869x, (1979).
Danieli, et al., Chemical Abstracts, vol. 77, 19862u, (1972).
Danieli, et al., Chemical Abstracts, vol. 82, 140,362n, (1975).
Danieli, et al., Chemical Abstracts, vol. 91, 20858t, (1979).
Danieli, et al., Chemical Abstracts, vol. 92, 129160f, (1980).
Atta-ur-Rahman, et al., Chemical Abstracts, vol. 93, 95472n, (1980).
Toth, et al., Annalen, 1977, No. 4, pp. 529-536, (1977).
Kokosi, et al., Tetrahedron Letters, vol. 22, No. 48, pp. 4861-4862, (1981).
Terzyan, et al., Chemical Abstracts, vol. 62, 11868c, (1965).
Horvath-Dora, et al., Chemical Abstracts, vol. 88, 191200q, (1978).
Chinoin-Gyogyszer, Chemical Abstracts, vol. 96, 104584s, (1982).
Kokosi, et al., Chemical Abstracts, vol. 97, 24059e, (1982).
Hermecz, et al., Chemical Abstracts, vol. 97, 127863s, (1982).
Hermecz, et al., Int. Conf. Chem. Biotechnol. Biol. Act. Nat. Prod., (Proc.), 1st 1981, 3(2), pp. 69-72, (1981).
Correa, et al., Chemical Abstracts, vol. 84, 14678y, (1976).
Kametani, Chemical Abstracts, vol. 92, 163996t, (1980).
Kametani, et al., Heterocycles 4, pp. 1487-1492, (1976).
Kametani, et al., Heterocycles, vol. 4, pp. 23-28, (1976).
Raymond-Hamet, et al., Compt. Rend. 220 792, (1945).
Raymond-Hamet, et al., Compt. Rend 255, 1152-1154, (1962).
Li, et al., Chemical Abstracts, vol. 65, 3922d, (1966).
Sugusawa, et al., Chemical Abstracts, vol. 34, 7291, 4-5, (1940).
Clauder, et al., Acta-Chim. Acad. Sci. 72, pp. 221-230, (1972).
Asahina, et al., J. Chem. Soc. 1927, pp. 1708-1711.
Schöpf, Angew. Chem. 50, pp. 797-805, (1937).
Beilstein, E. II, 26, H26, 189-191, pp. 104-105.
Article entitled "Short Communications Syntheses And Enzymatic Transformations" and Biosyntheses, vol. 3$_2$.
Náray-Szabó, et al., J. Chem. Soc., Perkin, I (1974), p. 1753.
Carboni, Chem. Abstracts, 50, 16767, (1956).
Kataguri, et al., J. Org. Chem. 47, 167-169, (1982).

Primary Examiner—Donald G. Daus
Assistant Examiner—Diana G. Rivers
Attorney, Agent, or Firm—Karl F. Ross; Herbert Dubno

[57] ABSTRACT

New Rutecarpine analogs are disclosed having Rutecarpine-like activity, especially diuretic activity. Also a novel process for the preparation of the Rutecarpine analogs is disclosed.

28 Claims, No Drawings

INDOLO[2',3';3,4]PYRIDO[2,1-B]QUINAZOLINE-5-ONES, A PROCESS FOR THE PREPARATION THEREOF, AND DIURETIC COMPOSITIONS AND METHODS USING THEM

The present invention relates to a new indolo[2',3';3,4]pyrido[2,1-b]quinazoline-5-ones, acid-addition salts thereof and a process for the preparation thereof. The new compounds of the formula (I)

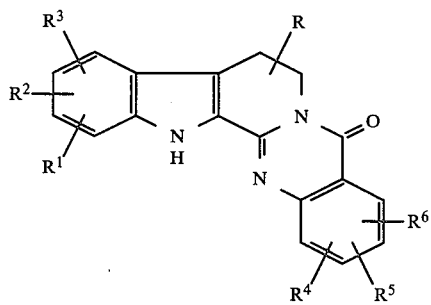

are new substituted derivatives of Rutecarpine of the formula (III)

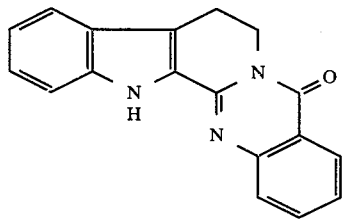

(J. Pharm. Soc. Japan, 405, 1293; 1915) known from the world of plants and used as a diuretic and respiration and blood circulation influencing agent (Yao Hsueh Hsueh Pao, 13, 265, 1966; Compt. rend. 220, 792, 1945; 255, 1152, 1962). The compounds of the formula (I) may be used as pharmaceutically active ingredients of Rutecarpine-like activity as mentioned above.

Rutecarpine of the formula (III) can be prepared by forming the basic structure of indolo[2',3';3,4-]pyrido[2,1-b]quinazoline-5-one by reacting 1,2,3,4-tetrahydro-norharman-1-one or 3,4-dihydro-beta-carboline with a derivative of anthranylic acid (J. Pharm. Soc. Japan, 543, 51, 1927; 60, 311, 1940; J. Chem. Soc. 1927, 1710; Angew. Chem. 50, 779, 1937; Acta Chim. Hung. 72, 221, 1972; Heterocycles 4, 23, 1975; 4, 1487, 1976; J. Am. Chem. Soc. 98, 6186, 1976; 99, 2306, 1977).

According to the invention indolo[2',3';3,4-]pyrido[2,1-b]-quinazoline-5-ones—of the formula (I)—wherein R stands for hydrogen or $C_{1-4}$ alkyl, $R^1$, $R^2$ and $R^3$ are the same or different and stand for hydrogen(s), halogen(s), $C_{1-4}$ alkyl, $C_{1-4}$ alkoxy, phenyl, cyano, trifluoromethyl, $C_{1-4}$ alkanoyl, nitro, carboxy, $C_{2-5}$ alkoxycarbonyl, amino, $C_{1-4}$ alkanoyl amino, phenyloxy, hydroxy, $C_{1-4}$ alkylamino, $C_{1-4}$ alkyl containing dialkylamino, carbamoyl, $C_{7-12}$ aralkoxy, carbohydrazido, alkylaminocarbonyl of 1-4 carbon atoms in the alkyl group, dialkylaminocarbonyl(s) containing 1-4 carbon atoms in the alkyl part, or optionally $R^1$ and $R^2$ together form methylenedioxy or —(CH=CH)$_2$ attached to two adjacent carbon atoms of the benzene ring, $R^4$, $R^5$ and $R^6$ are the same or different and stand for hydrogen(s), halogen(s), $C_{1-4}$ alkyl, $C_{1-4}$ alkoxy, phenyl, cyano, $C_{1-4}$ alkanoyl, nitro, carboxy, $C_{2-5}$ alkoxycarbonyl, amino, $C_{1-4}$ alkanoyl amino, hydroxy, $C_{1-4}$ alkylamino, dialkylamino containing 1-4 carbon atoms in the alkyl part, carbamoyl, $C_{7-12}$ aralkoxy, carbohydrazido, $C_{1-4}$ alkylaminocarbonyl, dialkylaminocarbonyl group(s) containing 1-4 carbon atoms in the alkyl part or optionally $R^4$ and $R^5$ together form methylenedioxy attached to two adjacent carbon atoms of the benzene ring, and the dotted lines represent optionally further chemical bonds with the proviso that if the dotted lines represent further chemical bonds then R, $R^1$, $R^2$, $R^3$, $R^4$, $R^5$ and $R^6$ cannot simultaneously stand for hydrogen and if $R^1$ is attached to the 10-position of the [2',3';3,4]pyrido[2,1-b]quinazoline-structure then it does not stand for methoxy, benzyloxy, hydroxy or methoxycarbonyl, and if R, $R^1$, $R^2$, $R^3$, $R^6$ stand for hydrogen and $R^4$ is attached to position 2 and $R^5$ to position 3 and $R^5$ is methoxy then $R^4$ does not represent hydrogen, hydroxy, benzyloxy, or methoxy and if R, $R^1$, $R^2$, $R^3$, $R^5$ and $R^6$ stand for hydrogen and $R^4$ is attached to position 1 then it does not stand for hydroxy or methoxy and if R, $R^2$, $R^3$, $R^6$ stand for hydrogen and $R^1$ is attached to position 10 and stands for methoxy and $R^4$ is attached to position 2 and $R^5$ to position 3 then they cannot simultaneously stand for methoxy, and if R, $R^1$, $R^2$, $R^3$ and $R^6$ stand for hydrogen and $R^4$ is attached to position 2 and $R^5$ to position 3 then they cannot together form methylenedioxy, and if R, $R^1$, $R^2$, $R^3$, $R^5$ and $R^6$ stand for hydrogen and $R^4$ is attached to position 2 then it does not stand for methoxy. The compound of the formula (I) and acid-addition salts thereof may be prepared with good yield from 6-phenyl-hydrazono-6,7,8,9-tetrahydro- and 6-phenyl-hydrazono-1,2,3,4,6,7,8,9-octahydro-1H-pyrido[2,1-b]quinazoline-11-ones or acid-addition salts thereof—of the formula (II)

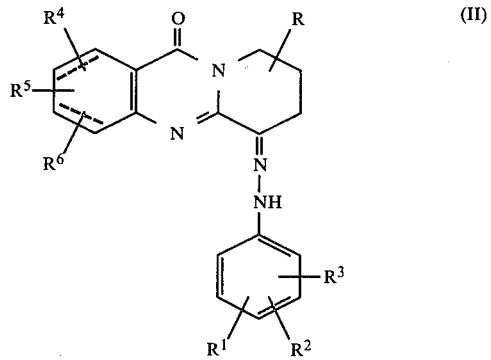

wherein R, $R^1$, $R^2$, $R^3$, $R^4$, $R^5$ and $R^6$ are as defined above and the dotted lines are optionally present further chemical bonds—under the conditions of the synthesis according to Fischer (Chem. Rev. 63, 373, 1963; 69, 230, 1969; Tetrahedron 36, 161, 1980).

According to a preferred embodiment of the process of the invention pyrido-quinazolines of the formula (II) are heated in a mineral acid, organic acid or Lewis acid and optionally in the presence of a solvent.

As a solvent alkanols (such as methanol, ethanol), water, aromatic hydrocarbons (benzene, toluene, xylene), ethers (diethyl ether, dioxan, tetrahydrofuran), halogenated hydrocarbons (chloroform, carbon tetrachloride, chlorobenzene) etc. may be used.

As acids mineral acids, such as hydrogen chloride, hydrogen bromide, hydrogen iodide, sulphuric acid, phosphoric acid, polyphosphoric acid and organic acids, such as alkane carboxylic acids (formic acid, acetic acid, oxalic acid, propionic acid), aromatic hydroxy derivatives (phenol) and Lewis acids, such as metal halids (zinc chloride, zinc bromide, aluminum chloride, copper chloride, copper bromide, nickel chloride, platinum chloride, cobalt chloride, stannous chloride, beryllium chloride, magnesium chloride, borontrifluoride) may be used. In the synthesis amine salts (aniline hydrochloride), alkane carboxylic acid halides (acetyl chloride, propionyl chloride), Grignard reactants (phenyl magnesium chloride, phenyl magnesium bromide, ethyl magnesium bromide, methyl magnesium iodide), ion exchanger in H form (Amberlite 1R-120) and metal powder (copper powder, nickel powder, cobalt powder) may also be employed.

The above mentioned catalysts may preferably be combined. Thus a mixture of sulphuric acid-alkane carboxylic acid (sulphuric acid-acetic acid) hydrogen halide-alkane carboxylic acid (hydrochloride-acetic acid, hydrogen bromide-acetic acid), boron trifluoride-alkane carboxylic acid (boron trifluoride etherate-acetic acid), metal halide-alkane carboxylic acid (nickel chloride-acetic acid), metal halide-hydrohalide) (stannous chloride-hydrochloride) may be employed.

The reaction may be performed at a temperature depending on the used catalyst and solvent.

A particularly preferred method of the invention comprises heating a pyrido-quinazoline derivative of the formula II or acid addition salt thereof in poly-phosphoric acid at 100°–220° C. (preferably 140° to 210°) by using 5–20 parts by weight of polyphosphoric acid related to 1 part by weight of pyrido-quinazoline of the formula II. The reaction is preferably performed for 5 to 120 minutes.

The formed indolo [2',3',3, 4]pyrido[2,1-b]quinazole-5-ones of the formula I may be isolated conventionally by diluting the reaction mixture, cooled preferably to room temperature, with water and by removing the product precipitating in crystals e.g. by filtration, centrifuging etc.

A group $R^1$, $R^2$, $R^3$, $R^4$, $R^5$ and/or $R^6$ may be, if desired, converted by methods known per se to another group $R^1$, $R^2$, $R^3$, $R^4$, $R^5$ and/or $R^6$. Thus for example if one of the above substituents stands for carboxy then it may be converted to ester with a given alcohol. Esterification may be carried out by known esterification processes. One may preferably proceed by introducing to an alcoholic solution dry hydrogen chloride gas whereupon the esterification takes place or a mixture of the carboxylic acid and of the alcohol may be heated in the presence of concentrated sulphuric acid and optionally the formed water can be removed by azeotropic distillation, with benzene or chloroform or it may be converted to acid amide through an active ester e.g. by using triethylamine, or chloroformate and ammonia or it may be reacted with other amines to form N-substituted or N,N-disubstituted amines or decarboxylated by heating preferably in pyridine, quinoline or polyphosphoric acid.

If at least one of the groups $R^1$, $R^2$, $R^3$, $R^4$, $R^5$ and/or $R^6$ stands for ester then it may be reesterified with a different alcohol preferably in the presence of hydrogen chloride, it may be converted to amide with ammonia preferably in the presence of an alcohol, or to carbohydrazide with hydrazine hydrate whereas N-substituted or N,N-disubstituted acid amides are formed by reaction with amines.

The substituted acid amide derivative may optionally be prepared by converting a compound of the formula I wherein at least one of $R^1$, $R^2$, $R^3$, $R^4$, $R^5$ and/or $R^6$ stands for carboxy to acid halide by methods known per se e.g. by using thionyl chloride, phosphoryl bromide, phosphorus pentachloride—and by reacting the obtained acid halide with a suitable amine or with ammonia.

If at least one of $R^1$, $R^2$, $R^3$, $R^4$, $R^5$ and/or $R^6$ stands for acid amide then it may be converted to a nitrile group e.g. by binding water with phosphoryl chloride, phosphorus pentoxide or thionyl chloride.

If at least one of $R^1$, $R^2$, $R^3$, $R^4$, $R^5$ and/or $R^6$ stands for nitrile, ester or acid amide then said groups may, if desired, be converted to a carboxyl group by acid or alkaline hydrolysis.

If at least one of $R^1$, $R^2$, $R^3$, $R^4$, $R^5$ and/or $R^6$ stands for alkoxy then it may be dealkylated by methods known per se—e.g. by heating in concentrated hydrogen bromide solution—to hydroxy.

If at least one of $R^1$, $R^2$, $R^3$, $R^4$, $R^5$ and/or $R^6$ stands for hydroxy then it may be converted to alkoxy by methods known per se. The alkylation may be carried out by using diazoalkanes such as diazomethane, diazoethane or by using alkyl halides in the presence of acid binding agent such as triethyl amine, sodium hydroxide or sodium carbonate.

If at least one of $R^1$, $R^2$, $R^3$, $R^4$, $R^5$ and/or $R^6$ stands for nitro, then it may be converted to amino by methods known per se. The amino group may preferably be formed by catalytic reduction, in the presence of palladium, active coal or Raney nickel catalyst by hydrogenation and the amino group may optionally be converted to acylamino by using acid halide, acid anhydride etc.

The present invention also extends to optically active isomers of the compounds of the formula I.

Optical isomerism may occur, if in the formula I R stands for $C_{1-4}$ alkyl.

The obtained indolo[2',3';3,4]pyrido[2,1-b]quinazoline-5-ones are, if desired, optionally converted to acid addition salts by methods known per se.

A preferred group of the compounds of formula (I) includes those compounds where R is hydrogen or $C_1$ to $C_4$ alkyl, $R^1$, $R^2$, $R^4$, $R^5$ and $R^6$ are each hydrogen and $R^3$ is $C_1$ to $C_4$ alkyl, halogen, cyano, or phenoxy. Preferably the $R^3$ substituent is attached to the 10-position of the Rutecarpine skeleton. In this preferred group of compounds the dotted lines each represent an additional carbon-carbon bond.

Another preferred group of compounds of formula (I) includes those compounds where R is hydrogen or $C_1$ to $C_4$ alkyl, $R^1$, $R^2$ and $R^3$ are hydrogen, $C_1$ to $C_4$ alkyl or halogen, and $R^4$, $R^5$ and $R^6$ are each hydrogen. In the preferred group of compounds the dotted lines do not represent additional carbon-carbon bonds and the carbon atoms represented at either end of the dotted lines are fully saturated.

The pyrido-quinazolines of the formula (II) used as starting materials may be prepared generally by a diazo-coupling reaction of 6,7,8,9-tetrahydro-11H- or 1,2,3,4,6,7,8,9-octahydro-11H-pyrido[2,1-b]quinazoline-11-ones of the formula (IV)

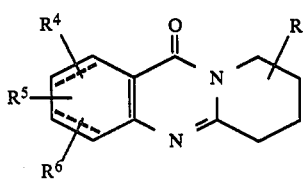

with phenyl diazonium chloride of the formula (V)

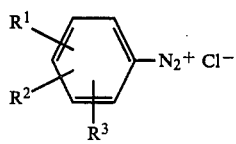

The diazo-coupling reaction can be carried out by methods known per se preferably in aqueous acetic acid medium. 6,7,8,9-Tetrahydro-11H- and 1,2,3,4,6,7,8,9-octahydro-11H-pyrido[2,1-b]quinazoline-11-ones are known compounds and may be prepared for example from a 2-piperidone derivative and a suitable anthranylic derivative (J. Am. Chem. Soc. 99, 2306, 1977).

The compounds of the formula (I) may be used as active ingredients of pharmaceutical compositions due to their biologica activity. The compounds show diuretic and blood circulation and respiration effecting activity.

Pharmacological test results:

Diuretic activity of the compounds is shown in Table 1. Tests were carried out on CFY rats of both sexes. The test substance was administered per os in a 1% methyl cellosolve suspension. Each group consisted of 3 animals of the same sex.

TABLE 1

| Substance Code | Sex of rat | Dosage | Combined urine (ml/100 bwt) | | |
|---|---|---|---|---|---|
| | | | 0–5 h | 5–24 h | 0–24 h |
| A | female | 5 mg | 1.24 | 3.81 | 5.05 |
| | male | | 1.73 | 4.35 | 6.08 |
| B | female | 5 mg | 2.70 | 7.96 | 10.66 |
| | male | | 2.81 | 5.61 | 8.42 |
| C | female | 5 mg | 3.31 | 9.80 | 13.11 |
| | male | | 3.86 | 10.39 | 14.25 |

Compound A: methyl cellosolve
Compound B: Hypothiazide
Compound C: 1,2,3,4,7,8-Hexahydro-5H—13H—indolo[2',3';3,4]pyrido-[2,1-b]quinazoline The compositions may be formulated to a form suitable for oral or parenteral route of administration e.g. to tablets, dragées, capsules, powder mixture, aerosol spray, aqueous suspension, or solution or injectable solution or syrup. The compositions may contain solid diluents or carriers, sterile aqueous solvent or non-toxic organic solvent. The orally administered forms may contain the conventionally used sweetening or flavoring agents.

The orally administered tablets may contain as carrier lactose, sodium citrate, calcium carbonate and disintegrating agents such as starch, alginic acid, lubricants such as talc, sodium lauryl sulphate, magnesium stearate. The capsules may contain lactose and polyethylene glycol as carrier. The aqueous suspension may include emulsifiers or suspending agents. The organic solvent suspension may be diluted with ethanol, glycerol ot chloroform.

The compositions suitable for inhalation and parenteral administration are suitable solutions or suspensions of the active ingredient in a suitable medium (e.g. peanut oil, sesame oil, polypropylene glycol or water). The injectable compositions may be administered intramuscularly, intravenously or subcutaneously. The injectable solutions may preferably be prepared in aqueous medium and the pH is adjusted to a suitable value. The solutions may be prepared, if necessary, in isotonic saline or glucose solution.

The daily dosage may vary within a wide range and depends upon the condition, age, weight of the patient and upon the formulation form and activity of the active ingredient. In case of oral administration the daily dosage is generally between 0.05–15 mg/kg while in case of intravenous administration the daily dosage is between 0.001–5 mg/kg in one single or several doses.

The above data are only informative and the doses may be below or above the given range depending upon the requirements of the given case and the prescriptions of the physician. Further details of the process are to be found in the following Examples which serve merely for illustration and not for limitation.

EXAMPLE 1

1 g of 6-[(4-Methyl-phenyl)-hydrazono]-6,7,8,9-tetrahydro-11H-pyrido[2,1-b]quinazoline-11-one is added in small portions to 10 g of polyphosphoric acid heated to 180° C. within 5 minutes. After adding the above substance the reaction mixture is stirred for 30 minutes at 180° C. After cooling the mixture is diluted to 40 ml of water and the pH of the solution is adjusted to 5 by adding 25 V/W% ammoniumhydroxide solution. The precipitated crystals are filtered and washed with water. After drying the product is dissolved in dimethylformamide and treated with active charcoal at 100° C. The dimethylformamide solution is diluted with water whereafter yellowish-white crystals are obtained which are filtered and washed with water. After drying 0.6 g (63%) of 10-methyl-7,8-dihydro-5H,13H-indolo[2',3';3,4]-pyrido[2,1-b]quinazoline-5-one are obtained.

Analysis for the formula $C_{19}H_{15}N_3O$: Calculated: C 75.72%, H 5.01%, N 13.94%, Found: C 75.43%, H 4.99%, N 14.05%.

EXAMPLE 2

1 g of 6-[(4-chloro-phenyl)-hydrazono]-6,7,8,9-tetrahydro-11H-pyrido[2,1-b]quinazoline-11-one is added to 10 g of polyphosphoric acid heated to 180° C. and the mixture is stirred for 20 minutes at this temperature. After cooling the mixture is diluted with 40 ml of water and the precipitate is filtered and washed with water. After drying the product is recrystallized from a mixture of dimethylformamide and ethyl acetate. 0.77 g (81%) of 10-chloro-7,8-dihydro-5H,13H-indolo[2',3';3,4]pyrido[2,1-b]quinazoline-5-one are obtained melting at 310° C. to 312° C.

Analysis for the formula $C_{18}H_{12}N_3OCl$: Calculated: C 67.19%, H 3.76%, N 13.05%, Cl 11.01%, Found: C 67.11%, H 3.74%, N 13.13%, Cl 10.97%.

EXAMPLE 3

1 g of 6-[(4-Fluoro-phenyl)-hydrazono]-6,7,8,9-tetrahydro-11H-pyrido[2,1-b]quinazoline-11-one is converted according to Example 2 and 0.75 g (79%) of 10-fluoro-7,8-dihydro-5H-13H-indolo[2',3';3,4]pyrido[2,1-b]quinazoline-5-one are obtained melting at 290° C.

Analysis for the formula $C_{18}H_{12}N_3OF$: Calculated: C 70.81%, H 3.96%, N 13.76%, Found: C 70.70%, H 3.94%, N 13.91%.

EXAMPLE 4

1 g of 6-[(4-Bromo-phenyl)-hydrazono]-6,7,8,9-tetrahydro-11H-pyrido[2,1-b]quinazoline-11-one is converted and processed according to Example 2 and 0.85 g of the named product are obtained which is dissolved in 10 ml of dimethylformamide and treated with active charcoal and applied to a column containing 15 g of Kieselgel of particle size 0.1–0.2 mm and eluted with ethyl acetate. 0.64 g (67%) of yellowish-white crystals of 10-bromo-7,8-dihydro-5H,13H-indolo[2',3';3,4-]pyrido[2,1-b]quinazoline-5-one are obtained melting at 284° C.

Analysis for the formula $C_{18}H_{12}N_3OBr$: Calculated: C 59.03%, H 3.30%, N 11.47%, Found: C 59.09%, H 3.22%, N 11.28%.

EXAMPLE 5

1 g of 6-[(4-Cyano-phenyl)-hydrazono]-6,7,8,9-tetrahydro-11H-pyrido[2,1-b]quinazoline-11-one is heated in 10 g of polyphosphoric acid at 180° C. for 30 minutes. After cooling the reaction mixture is diluted with 40 ml of water and the pH is adjusted to 5 by adding 25 V/W% ammoniumhydroxide solution. The precipitated product is filtered, washed with water and dried. 0.88 g (92%) of 10-cyano-7,8-dihydro-5H,13H-indolo[2',3';3,4]pyrido[2,1-b]quinazoline-5-one are obtained which after recrystallization from dimethylformamide melts at 255° C.

Analysis for the formula $C_{19}H_{12}N_4O$: Calculated: C 73.06%, H 3.87%, N 17.93%, Found: C 72.95%, H 3.86%, N 17.90%.

EXAMPLE 6

1 g of 6-(2-Naphthyl-hydrazono)-6,7,8,9-tetrahydro-pyrido[2,1-b]quinazoline-11-one is converted according to Example 5 and 0.85 g (89%) of 7,8-dihydro-5H,13H-indolo[2',3';2,3]pyrido[2,1-b]quinazoline-5-one are obtained melting at 298° C.

Analysis for the formula $C_{22}H_{15}N_3O$: Calculated: C 78.32%, H 4.48%, N 12.45%, Found: C 78.51%, H 4.60%, N 12.21%.

EXAMPLE 7

1 g of 6-[(4-Phenyloxy-phenyl)-hydrazono]-6,7,8,9-tetrahydro-pyrido[2,1-b]quinazoline-11-one is added to 15 g of polyphosphoric acid heated to 180° C. and the mixture is maintained at this temperature for 20 minutes. After cooling the reaction mixture is diluted with 50 ml of water and during cooling the pH is adjusted to 5 by adding a 25 V/W% ammoniumhydroxide solution. The precipitated product is filtered and washed with water. After drying, the mixture dissolved in 5 ml of dimethylformamide is applied to a column of diameter of 1 cm filled with 15 g of Kieselgel of particle size 0.1–0.2 mm and eluted with ethyl acetate. 0.4 g (41%) of 10-phenyloxy-7,8-dihydro-5H,13H-indolo[2',3';3,4-]pyrido[2,1-b]quinazoline-5-one are obtained which after recrystallization from ethyl acetate melts at 276°–278° C.

Analysis for the formula $C_{24}H_{17}N_3O_2$: Calculated: C 75.97%, H 4.51%, N 11.07%, Found: C 76.09%, H 4.55%, N 11.02%.

EXAMPLE 8

10 g of 6-phenyl-hydrazono-1,2,3,4,6,7,8,9-octahydropyrido[2,1-b]quinazoline-11-one are added to 100 g of polyphosphoric acid heated to 180° C. and the reaction mixture is heated for 30 minutes at this temperature until the gas evolution ceases. The mixture is then cooled to room temperature and diluted with 200 ml of water under steady cooling. The pH of the solution is adjusted to 5 by adding a 25 V/W% ammoniumhydroxide solution. The precipitated product is filtered and washed with water. After drying 8.8 g (93%) of 5-oxo-1,2,3,4,7,8-hexahydro-5H,13H-indolo[2',3';3,4-]pyrido[2,1-b]-quinazoline are obtained which after recrystallization from ethyl acetate melts at 259°–261° C.

Analysis for the formula $C_{18}H_{17}N_3O$: Calculated: C 74.20%, H 5.88%, N 14.42%, Found: C 74.08%, H 5.84%, N 14.48%.

EXAMPLE 9

1 g of 6-(4-Methyl-phenylhydrazono)-9-methyl-1,2,3,4,6,7,8,9-octahydro-pyrido[2,1-b]quinazoline-11-one is added to 10 g of polyphosphoric acid heated to 180° C. and the reaction mixture is heated for 40 minutes at this temperature. After cooling the mixture is diluted with 60 ml of water. A yellowish-white crystalline precipitate is obtained which is filtered and washed with water. After drying the obtained solid is dissolved in chloroform and the undissolved part is filtered off. The solution is treated with active charcoal and evaporated. The obtained yellowish-white oil is crystallized from ethyl acetate. 0.4 g of 7,10-dimethyl-5-oxo-1,2,3,4,7,8-hexahydro-5H,13H-indolo[2',3';3,4-]pyrido[2,1-b]quinazoline are obtained melting at 220° C.

Analysis for the formula $C_{20}H_{21}N_3O$: Calculated: C 75.20%, H 6.62%, N 13.15%, Found: C 75.11%, H 6.70%, N 13.22%.

EXAMPLE 10

1 g of 9-Methyl-6-(4-chloro-phenylhydrazono)-1,2,3,4,6,7,8,9-octahydro-pyrido[2,1-b]quinazoline-11-one is added to 10 g of polyphosphoric acid heated to 180° C. and the reaction mixture is heated for 30 minutes at this temperature. The reaction mixture is cooled when the gas evolution ceases and diluted with 40 ml of water whereupon a yellowish-white precipitate is formed. The precipitated product is filtered and washed with water. After drying, the product is crystallized from ethanol. 0.7 g of 7-methyl-10-chloro-5-oxo-1,2,3,4,7,8-hexahydro-5H,13H-indolo[2',3';3,4-]pyrido[3,2-a]quinazoline are obtained melting at 248° C.

Analysis for the formula $C_{19}H_{18}N_3OCl$: Calculated: C 67.15%, H 5.33%, N 12.36%, Cl 10.43%, Found: C 67.08%, H 5.37%, N 12.41%, Cl 10.35%.

EXAMPLE 11

1 g of 9-methyl-6-phenylhydrazono-1,2,3,4,6,7,8,9-octahydro-pyrido[2,1-b]quinazoline-11-one is added to 15 g of polyphosphoric acid heated to 170° C. and the mixture is stirred for 20 minutes at 180° C. After cooling, the dark melt is diluted with 50 ml of water. Greenish-yellow crystals are precipitated, which are filtered and washed with water. After drying, the product is recrystallized from ethanol. 0.4 g of 7-methyl-5-oxo-1,2,3,4,7,8-hexahydro-5H,13H-indolo[2',3';3,4-

]pyrido[2,1-b]quinazoline are obtained melting at 232° C.

Analysis for the formula $C_{19}H_{19}N_3O$: Calculated: C 74.72%, H 6.27%, N 13.75%, Found: C 74.66%, H 6.28%, N 13.83%.

EXAMPLE 12

1 g of 8-Methyl-6-phenylhydrazono-1,2,3,4,6,7,8,9-octahydro-pyrido[2,1-b]quinazoline-11-one is added to 10 g of polyphosphoric acid heated to 180° C. and the reaction mixture is stirred for 40 minutes at 180°–185° C. The mixture is then cooled to room temperature and diluted with 50 ml of water under cooling.

The precipitated crystals are filtered and washed with water. After drying, the obtained product is dissolved in 20 ml of chloroform and treated with active charcoal. After evaporating the chloroform solution the residual oil is crystallized from ethyl acetate. 0.6 g of 8-methyl-5-oxo-1,2,3,4,7,8-hexahydro-5H,13H-indolo[2',3';3,4]pyrido[2,1-b]quinazoline are obtained melting at 220°–221° C.

Analysis for the formula $C_{19}H_{19}N_3O$: Calculated: C 74.72%, H 6.27%, N 13.75%, Found: C 74.77%, H 6.31%, N 13.67%.

EXAMPLE 13

1 g of 6-(3,5-Dichloro-phenylhydrazono)-9-methyl-1,2,3,4,6,7,8,9-octahydro-pyrido[2,1-b]quinazoline-11-one is added to 10 g of polyphosphoric acid heated to 180° C. and the reaction mixture is heated for 50 minutes at 190° C. After cooling upon adding 50 ml of water, yellow precipitate is formed which is filtered and washed with water. The obtained product is crystallized from ethyl acetate after drying. 0.7 g of 9,11-dichloro-5-oxo-1,2,3,4,7,8-hexahydro-5H,13H-indolo[2',3';3,4]pyrido[2,1-b]quinazoline are obtained melting at 296°–297° C.

Analysis for the formula $C_{19}H_{17}N_3OCl_2$ Calculated: C 60.97%, H 4.57%, N 11.22%, Cl 18.94%, Found: C 60.82%, H 4.55%, N 11.10%, Cl 19.08%.

EXAMPLE 14

1000 g of 5-oxo-1,2,3,4,7,8-hexahydro-5H,13H-indolo[2',3';3,4]pyrido[2,1-b]quinazoline are homogenized with 1300 g of crystalline cellulose and with 140 g of amylopectine. The obtained homogenizate is granulated with 150 g Eudragit lac solution, regranulated after drying at 40° C. and homogenized with a powder mixture of 20 g magnesium stearate and 20 g of talc. The mixture is then compressed to tablets by methods known per se with adjusting the tablets to 250 mg.

EXAMPLE 15

750 mg of 10-methyl-7,8-dihydro-5H,13H-indolo[2',3';3,4]pyrido[2,1-b]quinazoline-5-one are homogenized with 1050 g of crystalline cellulose and 140 g of amylopectine. The mixture is then granulated with 150 mg of Eudragit lac solution and after drying at 40° C. and after regranulating the mixture is homogenized with a powder mixture of 20 g magnesium stearate and 20 g of talc, and compressed to 200 mg tablets.

The following are Examples directed to the preparation of the starting materials of the formula (II).

EXAMPLES 16–37

0.1 mole aniline derivative is admixed with 5 ml of 28 V/W% of hydrochloric acid solution of 1:1 dilution and the mixture is cooled to −5° C. A solution of 0.69 g (0.01 mole) sodium nitrate in 5 ml of water is slowly added dropwise under steady stirring and cooling. The reaction mixture is then stirred for 30 minutes at a temperature ranging from −5° C. to 0° C., whereafter the pH of the reaction mixture is adjusted to pH=4 by adding sodium acetate. The mixture is diluted with 5 ml glacial acetic acid and a solution of 2.0 g (0.01 mole) 11-oxo-6,7,8,9-tetrahydro-11H-pyrido[2,1-a]quinazoline in 10 ml of 50 Vol% acetic acid is added dropwise. The reaction mixture is stirred for 3 hours at −5° C. to 0° C. The mixture is then allowed to stand overnight in a refrigerator. The precipitated crystals are filtered and washed with water. The obtained 6-phenylhydrazono-11-oxo-6,7,8,9-tetrahydro-11H-pyrido[2,1-b]quinazolines are purified if necessary by recrystallization from n-propanol. The prepared compounds are summarized in Table 2.

EXAMPLES 38–39

One may proceed as disclosed in Examples 16–37 but as starting material 11-oxo-1,2,3,4,6,7,8,9-octahydro-11H-pyrido[2,1-b]quinoline is used instead of 11-oxo-6,7,8,9-tetrahydro-11H-pyrido[2,1-b]quinazoline.

The prepared compounds are summarized in Table 3.

TABLE 2

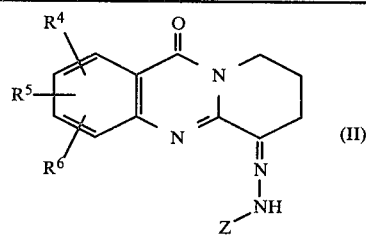

(II)

| | Compound of formula (II) | | | | | Mp. | Yield % | Empirical formula | Analysis % | | | | | |
|---|---|---|---|---|---|---|---|---|---|---|---|---|---|---|
| | | | | | | | | | calculated | | | found | | |
| Example | $R^4$ | $R^5$ | $R^6$ | R | Z | | | | C | H | N | C | H | N |
| 16 | H | H | H | H | Ph | 182–184 | 90 | $C_{18}H_{16}N_4O$ | 71.03 | 5.29 | 18.41 | 70.97 | 5.27 | 18.28 |
| 17 | H | H | H | H | 4-Cl—Ph | 191–192 | 94 | $C_{18}H_{15}N_4OCl$ | 63.81 | 4.46 | 16.53 | 64.01 | 4.57 | 16.25 |
| 18 | H | H | H | H | 4-Me—Ph | 187–188 | 88 | $C_{19}H_{18}N_4O$ | 71.67 | 5.69 | 17.59 | 72.13 | 5.60 | 17.48 |
| 19 | H | H | H | H | 4-Br—Ph | 180–183 | 84 | $C_{18}H_{15}N_4OBr$ | 56.41 | 3.94 | 14.61 | 56.24 | 3.85 | 14.51 |
| 20 | H | H | H | H | 4-$CF_3$—Ph | 195–197 | 83 | $C_{19}H_{15}N_4OF_3$ | 61.28 | 4.06 | 15.04 | 61.89 | 4.12 | 14.86 |
| 21 | H | H | H | H | 4-PhO—Ph | 178–180 | 83 | $C_{24}H_{20}N_4O_2$ | 72.71 | 5.08 | 14.13 | 72.50 | 4.96 | 14.07 |
| 22 | H | H | H | H | 3-Cl—Ph | 181–183 | 89 | $C_{18}H_{15}N_4OCl$ | 63.81 | 4.46 | 16.53 | 63.95 | 4.58 | 16.65 |
| 23 | 3-Cl | H | H | H | Ph | 219–222 | 65 | $C_{18}H_{15}N_4OCl$ | 63.81 | 4.46 | 16.53 | 63.84 | 4.56 | 16.71 |

TABLE 2-continued

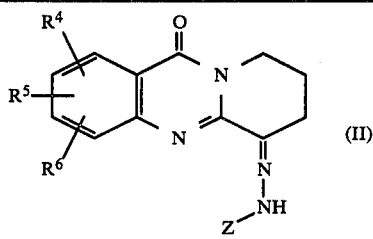

| Example | R⁴ | R⁵ | R⁶ | R | Z | Mp. | Yield % | Empirical formula | Analysis % calculated C | H | N | found C | H | N |
|---|---|---|---|---|---|---|---|---|---|---|---|---|---|---|
| 24 | 3-Cl | H | H | H | 4-Cl—Ph | 227 | 64 | $C_{18}H_{14}N_4OCl_2$ | 58.08 | 3.79 | 15.05 | 58.04 | 3.73 | 14.72 |
| 25 | H | H | H | 9-Me | Ph | 185–186 | 75 | $C_{19}H_{18}N_4O$ | 71.67 | 5.69 | 17.59 | 71.52 | 5.66 | 17.53 |
| 26 | H | H | H | H | 1-naphthyl | 192–193 | 86 | $C_{22}H_{18}N_4O$ | 70.57 | 4.84 | 14.96 | 70.55 | 4.84 | 14.40 |
| 27 | H | H | H | H | 2-naphthyl | 220 | 96 | $C_{22}H_{18}N_4O$ | 70.57 | 4.84 | 14.96 | 70.33 | 4.65 | 14.87 |
| 28 | H | H | H | H | 4-Ac—Ph | 255 | 81 | $C_{20}H_{18}N_4O_2$ | 69.34 | 5.23 | 16.17 | 69.33 | 5.35 | 16.28 |
| 29 | 3-Cl | H | H | H | 4-Me—Ph | 231 | 64 | $C_{19}H_{17}N_4OCl$ | 58.72 | 4.65 | 14.42 | 58.88 | 4.78 | 15.18 |
| 30 | H | H | H | H | 4-HO—Ph | 225(b) | 84 | $C_{18}H_{17}N_4O_2Cl$ | 60.59 | 4.80 | 15.70 | 60.69 | 4.85 | 15.86 |
| 31 | H | H | H | H | 4-MeO—Ph | 223 | 92 | $C_{19}H_{19}N_4O_2Cl$ | 61.53 | 5.16 | 15.10 | 62.10 | 5.23 | 14.90 |
| 32 | H | H | H | H | 4-NO₂—Ph | 250(b) | 92 | $C_{18}H_{16}N_5O_3Cl$ | 56.17 | 4.18 | 18.19 | 56.04 | 4.19 | 18.89 |
| 33 | H | H | H | H | 4-F—Ph | 245 | 90 | $C_{18}H_{16}N_4OFCl$ | 60.25 | 4.49 | 15.61 | 60.59 | 4.46 | 15.02 |
| 34 | H | H | H | H | 4-HOOC—Ph | 298(b) | 91 | $C_{19}H_{16}N_4O_3 \cdot HCl$ | 59.30 | 4.45 | 14.55 | 59.39 | 4.60 | 14.52 |
| 35 | H | H | H | H | 3-pyridyl | 188 | 23 | $C_{17}H_{15}N_5O \cdot HCl$ | 59.74 | 4.72 | 20.49 | 59.97 | 4.65 | 20.51 |
| 36 | H | H | H | H | 4-CN—Ph | 217 | 82 | $C_{19}H_{15}N_5O \cdot HCl$ | 62.38 | 4.41 | 19.14 | 62.24 | 4.50 | 19.32 |
| 37 | 2-MeO | 3-MeO | H | H | Ph | 230(b) | 66 | $C_{20}H_{20}N_4O_3$ | 65.92 | 5.53 | 15.37 | 65.72 | 5.26 | 15.21 |

TABLE 3

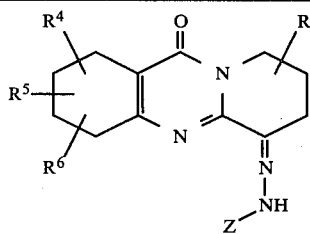

| Example | R⁴ | R⁵ | R⁶ | R | Z | Mp. | Yield | Empirical formula | Analysis % calculated C | H | N | found C | H | N |
|---|---|---|---|---|---|---|---|---|---|---|---|---|---|---|
| 38 | H | H | H | H | Ph | 205–208 | 85 | $C_{18}H_{20}N_4O$ | 70.10 | 6.53 | 18.16 | 69.93 | 6.51 | 18.07 |
| 39 | H | H | H | 9-Me | Ph | 190–193 | 83 | $C_{19}H_{22}N_4O$ | 70.78 | 6.87 | 17.37 | 70.55 | 6.91 | 17.27 |

EXAMPLE 40

10.8 g. (0.03 mole) 6,6-Dibromo-6,7,8,9-tetrahydro-11-oxo-11H-pyrido[2,1-b]quinazoline and 13.0 g. (0.12 mole] of phenyl hydrazine are heated in 120 ml ethanol for 4 hours. The precipitated crystals are filtered after cooling. When evaporating the mother liquor further crystals are precipitating, which are filtered and washed with some alcohol. The combined filtered product is suspended in 150 ml. of water containing 8.4 g. (0.06 mole) of sodium acetate whereafter it is filtered and washed with water. 8.4 g. (81%) of 6-phenylhydrazono-6,7,8,9-tetrahydro-11-oxo-11H-pyrido[2,1-b]quinazoline are obtained which after recrystallization from isopropanol melts at 177°–179° C. and which does not give a degression of melting point when admixed with the product according to Example 16.

EXAMPLE 41

3.74 g (0.01 mole) of 6,6-dibromo-9-methyl-11-oxo-6,7,8,9-tetrahydro-11H-pyrido[2,1-b]quinazoline and 4.32 g. (0.04 mole) of phenyl hydrazine are heated in 40 ml. of ethanol for 10 hours. The precipitated crystals are filtered after cooling. The filtered product is suspended in 100 ml. water containing 2.72 g. (0.02 mole), sodium acetate, filtered and washed with water. 2.4 g. (75%) orange 6-phenylhydrazono-9-methyl-11-oxo-6,7,8,9-tetrahydro-11H-pyrido[2,1-b]quinazoline are obtained which after recrystallization from ethanol melts at 185°–187° C.

Analysis for the formula $C_{19}H_{18}N_4O$: calculated C 71.67%, H 5.69%, N 17.59%, found: C 71.62%, H 5.58%, N 17.55%.

EXAMPLE 42

2.79 g. (0.01 mole) of 6-bromo-11-oxo-6,7,8,9-tetrahydro-11H-pyrido[2,1-b]quinazoline and 2.16 g. (0.02 mole) of phenyl hydrazine are heated in 30 ml. of ethanol for 6 hours at 80° C. Ethanol is then concentrated to a third volume. The mixture in then allowed to crystallize in an ice-box. The precipitated yellow crystals are filtered, and washed with ethanol and water. 2.1 g. (69%) of 6-phenyl-hydrazono-11-oxo-6,7,8,9-tetrahydro-pyrido-[2,1-b]quinazoline are obtained which after recrystallization from isopropanol melts at 179°–180° C. which when admixed with the product according to Example 16 or Example 40 does not give any melting point degression.

Analysis for the formula $C_{18}H_{16}N_4O$: calculated: C 71.03%, H 5.29%, N 18.41% found: C 70.88%, H 5.25%, N 18.38%.

EXAMPLE 43

0.93 g. (0.9 ml., 0.01 mole) of aniline are dissolved in 5 ml. 38 V/W% of hydrochloric acid of 1:1 dilution and the solution is cooled to −5° C. A solution of 0.65 g. (0.01 mole) sodium nitrite in 5 ml. water is added dropwise under steady cooling and stirring. The reaction mixture is stirred for 30 minutes at a temperature of −5° C. to 0° C. whereafter the pH of the solution is adjusted to pH=4 by adding sodium acetate and it is diluted with 10 ml. of acetic acid. To the solution of the diazonium salt a solution of 2.55 g. of 9-(dimethylaminomethylene)-11-oxo-6,7,8,9-tetrahydro-11H-pyrido[2,1-b]quinazoline in 25 ml. of dimethylformamide is slowly added dropwise at −5° C. The reaction mixture is stirred at 0° C. for 3 hours whereafter it is allowed to stand overnight in an ice-box. The mixture is then diluted with water and the precipitated crystals are filtered and washed with water. 2.61 g (86%) of 6-phenyl-hydrazono-6,7,8,9-tetrahydro-11-oxo-11H-pyrido[2,1-b]-quinazoline are obtained which after recrystallization from iso-propanol melts at 182°–184° C., and the product does not give any melting point degression when admixed with the product according to Example 16.

Analysis for the formula $C_{18}H_{16}N_4O$: calculated: C 71.03%, H 5.29%, N 18.41%, found: C 70.93%, H 5.24%, N 18.33%.

EXAMPLE 44

0.93 g. (0.01 mole) of aniline are dissolved in 5 ml. of 38 V/W% hydrochloric acid of a dilution of 1:1 and it is cooled to −5° C. A solution of 0.69 g. (0.01 mole) of sodium nitrite in 5 ml. of water is added dropwise under steady stirring and cooling. The reaction mixture is stirred for half an hour at −5° C. to 0° C. whereafter the pH of the solution is adjusted to pH=4 by adding sodium acetate and the solution is diluted with 10 ml. of acetic acid. To the reaction mixture a solution of 2.28 g. (0.01 mole) of 6-formyl-11-oxo-6,7,8,9-tetrahydro-11H-pyrido[2,1-b]quinazoline in 30 ml. of acetic acid is slowly added dropwise. The mixture is stirred for 1 hour at a temperature below 0° C. and the solution is then allowed to stand in the refrigerator. The precipitated crystals are filtered and washed with water. 3.1 g. (91%) of 6-phenyl-hydrazono-6,7,8,9-tetrahydro-11-oxo-11H-pyrido[2,1-b]quinazoline-hydrochloride are obtained melting at 255° C.

Analysis on the basis of $C_{18}H_{17}N_4OCl$: calculated: C 63.60%, H 5.04%, N 16.48%, Cl 10.16% found: C 63.44%, H 4.98% N 16.59%, Cl 10.11%.

EXAMPLES 45 TO 48

One may proceed as disclosed in Example 16–37 and as starting materials in Example 45 as pyrido[2,1-b]quinazoline derivative 2,3,4-trimethoxy-11-oxo-6,7,8,9-tetrahydro-11H-pyrido[2,1-b]quinazoline and in Example 46, 11-oxo-6,7,8,9-tetrahydro-11H-pyrido[2,1-b]quinazoline-2-carboxylic acid and in Example 47 ethyl-11-oxo-6,7,8,9-tetrahydro-11H-pyrido 2,1-b]quinazoline 2-carboxylate and in Example 48 11-oxo-6,7,8,9-tetrahydro-11H-pyrido[2,1-b]quinazoline is used and 6-phenylhydrazono 11-oxo-6,7,8,9-tetrahydro-11H-pyrido[2,1-b]quinazolines according to Table 4 are obtained. The products are recrystallized from n-propanol.

EXAMPLES 49 TO 59

One may proceed as disclosed in Examples 38 to 39 and as starting materials 11-oxo-1,2,3,4,6,7,8,9-octahydro-11H-pyrido[2,1-b]quinazolines are used which result in 6-phenyl-hydrazono-4 oxo-1,2,3,4,6,7,8,9-octahydro-11H-pyrido-[2,1-b]quinazolines according to Table 5.

In Examples 57 and 58 crystals precipitated from the diazo-coupling reaction mixture are suspended in a 5% V/W% sodium hydroxide solution and the aqueous solution is shaken out with choroform. The chloroform solution dried above anhydrous sodium sulphate is evaporated and the residue is crystallized.

EXAMPLE 60

0.46 g. (0.005 mole) of aniline are dissolved in 3 ml. of hydrochloric acid (36 V/W%) of a dilution of 1:1 and the solution is cooled to −5° C. A solution of 0.35 g. (0.005 mole) of sodium nitrite in 3 ml. of water is added dropwise. The reaction mixture is stirred for half an hour at −5° C. to 0° C. whereafter the pH of the solution is adjusted to 4 by adding sodium acetate. To the reaction mixture a solution of 1.23 g. (0.005 mole) of 6-formyl-11-oxo-1,2,3,4,6,7,8,9-octahydro-11H-pyrido-[2,1-b]quinazoline in 15 ml. 75 V% acetic acid is slowly added dropwise and the solution is stirred for 3 hours at a temperature below 0° C. whereafter the mixture is allowed to stand overnight in refrigerator and diluted with 30 ml. water. The precipitated crystals are filtered and washed with water. 1.3 g. (73%) of 6-phenyl-hydrazono-11-oxo-1,2,3,4,6,7,8,9-octahydro-11H-pyrido[2,1-b]quinazoline-hydrochloride are obtained melting at 242°–244° C.

Analysis for the formula $C_{19}H_{23}N_4OCl$: calculated: C 63.59%, H 6.46%, N 15.61%, Cl 9.88%, found: C 63.21%, H 6.28%, N 15.75%, Cl 9.65%.

TABLE 4

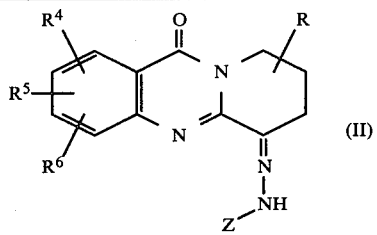

| Example | R⁴ | R⁵ | R⁶ | R | Z | Mp. | Yield % | Empirical formula | calculated C | H | N | found C | H | N |
|---|---|---|---|---|---|---|---|---|---|---|---|---|---|---|
| 45 | 2-OMe | 3-OMe | 4-OMe | H | Ph | 187–77 | 77 | $C_{21}H_{22}N_4O_4$ | 63.94 | 5.62 | 14.20 | 64.03 | 5.88 | 14.28 |
| 46 | 2-COOH | H | H | H | Ph | 257(b) | 30 | $C_{19}H_{16}N_4O_3$ | 65.51 | 4.62 | 16.08 | 65.56 | 4.66 | 16.01 |
| 47 | 2-COOEt | H | H | H | Ph | 201 | 85 | $C_{21}H_{20}N_4O_3$ | 67.00 | 5.35 | 14.88 | 67.03 | 5.45 | 14.85 |
| 48 | H | H | H | H | 4-EtOOC—Ph | 214 | 92 | $C_{21}H_{20}N_4O_3 \cdot HCl$ | 61.09 | 5.09 | 13.57 | 61.25 | 4.99 | 13.58 |

TABLE 5

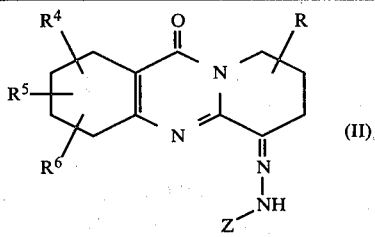

| Example | R⁴ | R⁵ | R⁶ | R | Z | Mp. | Yield % | Empirical formula | calculated C | H | N | found C | H | N |
|---|---|---|---|---|---|---|---|---|---|---|---|---|---|---|
| 49 | H | H | H | H | 4-Cl—Ph | 220 | 73 | $C_{18}H_{19}N_4OCl$ | 63.06 | 5.59 | 16.34 | 83.24 | 5.51 | 16.32 |
| 50 | H | H | 9-Me | H | 4-Cl—Ph | 207–208 | 70 | $C_{19}H_{21}N_4OCl$ | 63.95 | 5.93 | 15.70 | 64.14 | 6.17 | 15.76 |
| 51 | H | H | 9-Me | H | 4-NO₂—Ph | 168–170 | 79 | $C_{19}H_{21}N_5O_3HCl$ | 56.50 | 5.49 | 17.34 | 56.15 | 5.44 | 17.00 |
| 52 | H | H | H | H | 4-Me—Ph | 203–204 | 46 | $C_{19}H_{22}N_4O$ | 70.78 | 6.88 | 17.38 | 70.63 | 6.56 | 17.11 |
| 53 | H | H | 9-Me | H | 4-Me—Ph | 187–188 | 74 | $C_{20}H_{24}N_4O$ | 71.40 | 7.19 | 16.55 | 71.17 | 6.96 | 16.71 |
| 54 | H | H | 9-Me | H | 4-Et—Ph | 154–155 | 49 | $C_{21}H_{26}N_4O$ | 71.97 | 7.48 | 15.99 | 71.58 | 7.52 | 16.03 |
| 55 | H | H | 9-Me | H | 4-MeO—Ph | 161–162 | 42 | $C_{20}H_{24}N_4O_2$ | 68.16 | 6.86 | 15.90 | 68.43 | 6.95 | 15.80 |
| 56 | H | H | 9-Me | H | 2-naphthyl | 177–179 | 11 | $C_{23}H_{24}N_4O$ | 74.17 | 6.50 | 15.04 | 74.13 | 6.40 | 14.72 |
| 57 | H | H | 8-Me | H | Ph | 219 | 59 | $C_{19}H_{22}N_4O$ | 70.78 | 6.87 | 17.37 | 70.83 | 6.82 | 17.40 |
| 58 | H | H | 9-Me | H | 3,5-diCl—Ph | 227–228 | 33 | $C_{19}H_{20}N_4OCl_2$ | 58.33 | 5.15 | 14.31 | 56.40 | 5.23 | 14.27 |
| 59 | H | H | 7-Me | H | Ph | 200 | 59 | $C_{19}H_{22}N_4O$ | 70.78 | 6.87 | 17.37 | 70.91 | 6.75 | 17.46 |

We claim:

1. Process for the preparation of an indolo(2′,3′;3,4-)pyrido(2,1-b)quinazoline-5-one of the formula (I)

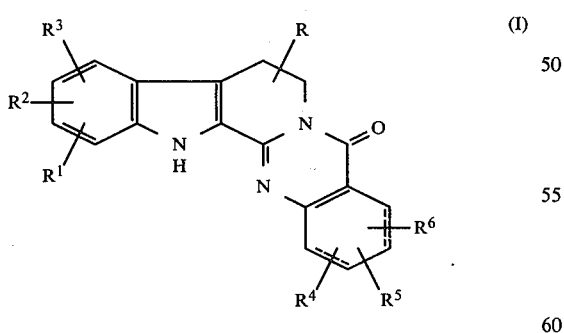

wherein

R stands for hydrogen or $C_{1-4}$ alkyl, $R^1$, $R^2$ and $R^3$ are the same or different and stand for hydrogen(s), halogen(s), $C_{1-4}$ alkyl, $C_{1-4}$ alkoxy, phenyl, cyano, trifuloromethyl, $C_{1-4}$ alkanoyl, nitro, carboxy, $C_{2-5}$ alkoxycarbonyl, amino, $C_{1-4}$ alkanoyl amino, phenyloxy, hydroxy, $C_{1-4}$ alkyl containing dialkylamino, carbamoyl, $C_{7-12}$ aralkoxy, carbohydrazido, alkylaminocarbonyl of 1-4 carbon atoms in the alkyl group, dialkylaminocarbonyl(s) containing 1-4 carbon atoms in the alkyl part, or optionally $R^1$ and $R^2$ together form methylenedioxy or —(CH=CH)₂ attached to two adjacent carbon atoms of the benzene ring, $R^4$, $R^5$ and $R^6$ are the same or different and stand for hydrogen(s), halogen(s), $C_{1-4}$ alkyl, $C_{1-4}$ alkoxy, phenyl, cyano, $C_{1-4}$ alkanoyl, nitro, carboxy, $C_{1-4}$ alkoxycarbonyl, amino, $C_{1-4}$ alkanoyl amino, hydroxy, $C_{1-4}$ alkylamino, dialkylamino containing 1-4 carbon atoms in the alkyl part, carbamoyl, $C_{7-12}$ aralkoxy, carbohydrazido, $C_{1-4}$ alkylaminocarbonyl, dialkylaminocarbonyl group(s) containing 1-4 carbon atoms of the benzene ring, and the dotted lines represent optionally present further chemical bonds, which comprises treating a 6-phenyl-hydrazono-11H-pyrido(2,1-b)quinazoline-11-one or a pharmaceutically acceptable acid-addition salt thereof of the formula (II)

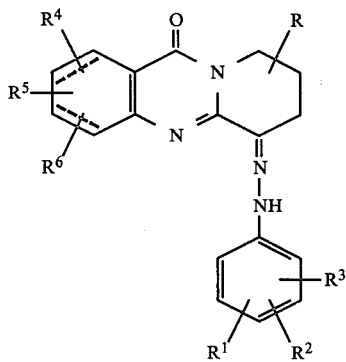

acid and converting the thus obtained indolo(2',3';3,4)pyrido(2,1-b)-quinazoline-5-one, if desired, to an acid-addition salt.

2. Process as claimed in claim 1 which comprises using organic, inorganic acids or Lewis acids as the acid.

3. Process as claimed in claim 2 which comprises using phosphoric acid, polyphosphoric acid, hydrochloric acid, hydrobromic acid or sulphuric acid as the acid.

4. Process as claimed in claim 2 which comprises using an alkane carboxylic acids, as the organic acid.

5. Process as claimed in claim 2 which comprises using as Lewis acid, aluminum chloride or zinc chloride.

6. Process as claimed in claim 1 which comprises using hydrochloride as acid-addition salt of the compound of formula (II).

7. Process as claimed in claim 1 which comprises heating a compound of the formula (II) or acid-addition salt thereof at a temperature ranging from 100° to 220° C.

8. Process as claimed in claim 7, which comprises heating a compound of formula (II) or hydrochloride salt thereof in the presence of polyphosphoric acid at a temperature ranging from 140° to 210° C.

9. A compound of the formula (I)

or a pharmaceutically acceptable acid addition salt thereof wherein
R is hydrogen or $C_1$ to $C_4$ alkyl; and
$R^1$, $R^2$ and $R^3$ are hydrogen, $C_1$ to $C_4$ alkyl, or halogen.

10. 5-oxo-1,2,3,4,7,8-hexahydro-5H,13H-indolo(2',3';3,4)-pyrido]2,1-b)quinazoline or a pharmaceutically acceptable acid addition salt thereof as defined in claim 9.

11. 7,10-dimethyl-5-oxo-1,2,3,4,7,8-hexahydro-5H,13H-indolo(2',3';3,4)pyrido(2,1-b)quinazoline or a pharmaceutically acceptable acid addition salt thereof as defined in claim 9.

12. 7-methyl-10-chloro-5-oxo-1,2,3,4,7,8-hexahydro-5H,13H-indolo(2',3';3,4)pyrido(2,1-b)quinazoline or a pharmaceutically acceptable acid addition salt thereof as defined in claim 9.

13. 8-methyl-5-oxo-1,2,3,4,7,8-hexahydro-5H,13H-indolo(2',3';3,4)pyrido(2,1-b)quinazoline or a pharmaceutically acceptable acid addition salt thereof as defined in claim 9.

14. 9,11-dichloro-5-oxo-1,2,3,4,7,8-hexahydro-5H,13H-indolo(2',3';3,4,)pyrido(2,1-b)quinazoline or a pharmaceutically acceptable acid addition salt thereof as defined in claim 9.

15. 7-methyl-5-oxo-1,2,3,4,7,8-hexahydro-5H,13H-indolo(2',3';3,4,)pyrido(2,1-b)quinazoline or a pharmaceutically acceptable acid addition salt thereof as defined in claim 9.

16. A diuretic composition comprising as active ingredient a pharmaceutically effective amount of a compound of the formula (I) as defined in claim 9 or a pharmaceutically acceptable acid addition salt thereof along with a pharmaceutically acceptable carrier.

17. A diuretic method of treatment which comprises the step of administering to an animal subject in need of said treatment a pharmaceutically effective amount of the compound of the formula (I) as defined in claim 9 or a pharmaceutically acceptable acid addition salt thereof.

18. A compound of the formula (I)

or a pharmaceutically acceptable acid addition salt thereof wherein
R is hydrogen or $C_1$ to $C_4$ alkyl; and
$R^3$ is $C_1$ to $C_4$ alkyl, halogen, cyano or phenoxy.

19. 10-methyl-7,8-dihydro-5H,13H-indolo(2',3';3,4,)-pyrido(2,1-b)quinazoline-5-one or a pharmaceutically acceptable acid addition salt thereof as defined in claim 18.

20. 10-chloro-7,8-dihydro-5H,13H-indolo(2',3';3,4)-pyrido(2,1-b)quinazoline-5-one or a pharmaceutically acceptable acid addition salt thereof as defined in claim 18.

21. 10-fluoro-7,8-dihydro-5H,13H-indolo(2',3';3,4,)-pyrido(2,1-b)quinazoline-5-one or a pharmaceutically acceptable acid addition salt thereof as defined in claim 18.

22. 10-bromo-7,8-dihydro-5H,13H-indolo(2',3';3,4,)-pyrido(2,1-b)quinazoline-5-one or a pharmaceutically acceptable acid addition salt thereof as defined in claim 18.

23. 10-cyano-7,8-dihydro-5H,13H-indolo(2',3';3,4)-pyrido(2,1-b)quinazoline-5-one or a pharmaceutically acceptable acid addition salt thereof as defined in claim 18.

24. 10-phenyloxy-7,8-dihydro-5H,13H-indolo(2',3';3,-4,)-pyrido(2,1-b)quinazoline-5-one or a pharmaceutically acceptable acid addition salt thereof as defined in claim 18.

25. A diuretic composition comprising as active ingredient a pharmaceutically effective amount of a compound of the formula (I) as defined in claim 18 or a pharmaceutically acceptable acid addition salt thereof along with a pharmaceutically acceptable carrier.

26. A diuretic method of treatment which comprises the step of administering to an animal subject in need of said treatment a pharmaceutically effective amount of the compound of the formula (I) as defined in claim 18 or a pharmaceutically acceptable acid addition salt thereof.

27. A compound of the Formula I

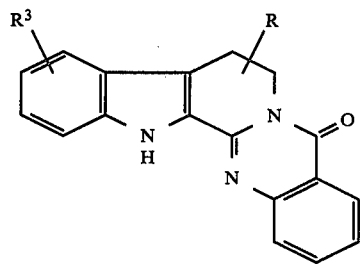

or a pharmaceutically acceptable acid addition salt thereof wherein
R is hydrogen or $C_1$ to $C_4$ alkyl and
$R^3$ is $C_1$ to $C_4$ alkyl.

28. The compound of the Formula I defined in claim 27 wherein $R^3$ is a substituent in the 10-position of the rutecarpine nucleus, and R is hydrogen.

* * * * *